(12) United States Patent
Patenaude

(10) Patent No.: US 8,631,931 B2
(45) Date of Patent: Jan. 21, 2014

(54) DENTAL PROSTHESIS AND DENTAL APPLIANCE STORAGE BOX

(76) Inventor: Danielle Patenaude, Laval (CA)

(*) Notice: Subject to any disclaimer, the term of this patent is extended or adjusted under 35 U.S.C. 154(b) by 564 days.

(21) Appl. No.: 12/908,072

(22) Filed: Oct. 20, 2010

(65) Prior Publication Data

US 2011/0308973 A1 Dec. 22, 2011

Related U.S. Application Data

(60) Provisional application No. 61/356,579, filed on Jun. 19, 2010.

(51) Int. Cl.
A61B 19/02 (2006.01)

(52) U.S. Cl.
USPC .......... 206/63.5; 220/9.1; 220/23.87

(58) Field of Classification Search
USPC ........ 206/818, 63.5, 368, 369, 438; 220/4.13, 220/527, 528, 23.87, 9.1
See application file for complete search history.

(56) References Cited

U.S. PATENT DOCUMENTS

| | | | | |
|---|---|---|---|---|
| 3,156,371 A * | 11/1964 | Harrison | ........................... | 220/6 |
| 3,248,167 A | 4/1966 | Friedman | | |
| 4,050,894 A | 9/1977 | Genis | | |
| 4,589,546 A * | 5/1986 | Sunderland | ............... | 206/315.11 |
| 5,266,763 A * | 11/1993 | Colombo | ..................... | 219/734 |
| 5,297,674 A * | 3/1994 | Birutis et al. | ................. | 206/214 |
| 5,967,305 A * | 10/1999 | Blonder et al. | ............... | 206/63.5 |
| 6,089,395 A * | 7/2000 | Karttunen et al. | .......... | 220/23.87 |
| 6,213,777 B1 * | 4/2001 | Seitzinger | ..................... | 433/229 |
| 7,648,041 B2 * | 1/2010 | Ueda et al. | ..................... | 220/378 |
| 2003/0178428 A1 * | 9/2003 | Chang | ............................ | 220/378 |
| 2005/0230465 A1 * | 10/2005 | Metzler et al. | ........... | 229/125.37 |
| 2009/0159607 A1 * | 6/2009 | Kratzer | ......................... | 220/849 |

FOREIGN PATENT DOCUMENTS

| | | |
|---|---|---|
| CA | 2314748 | 7/2001 |
| CA | 2112694 | 8/2004 |
| GB | 321028 | 10/1929 |
| GB | 362674 | 12/2011 |

OTHER PUBLICATIONS

PCT—International Search Report (ISR)—PCT/CA2011/000730 (Form PCT/ISA/210)—Oct. 12, 2011—5 pages.

* cited by examiner

Primary Examiner — Jacob K Ackun
(74) Attorney, Agent, or Firm — Benoît & Côté Inc.

(57) ABSTRACT

The present document describes a storage box for at least one of a dental prosthesis and a dental appliance. The storage box comprises: a container portion capable of holding a liquid; a holding area substantially within the container portion and for placing the at least one of a dental prosthesis and a dental appliance; a cover for placing over the container portion; and an external covering material substantially covering the container portion and the cover. In another embodiment, a separator divides the holding area in two or more parts. In another embodiment, the cover comprises a groove in which a seal can be lodged to hermetically seal the opening upon closure of the cover. The cover may also have a lip to hold liquid in the cover until the cover is sufficiently closed to release the liquid into the container.

11 Claims, 7 Drawing Sheets

DENTAL PROSTHESIS AND DENTAL APPLIANCE STORAGE BOX

CROSS-REFERENCE TO RELATED APPLICATIONS

This application claims priority under 35 USC §119(e) of U.S. provisional patent application 61/356,579, filed on Jun. 19, 2010, the specification of which is hereby incorporated by reference.

BACKGROUND (a) Field

The subject matter disclosed generally relates to utility storage boxes. More particularly, the present disclosure relates to storage boxes for personal dental articles.

(b) Related Prior Art

Storage boxes for personal dental articles such as dental prosthesis and dental appliances (e.g. orthodontic appliances) are known in the art. Some of the problems identified with such existing storage boxes include: the stored parts are not isolated from one another thereby resulting in potential damage to each part; and they cannot be carried around (e.g., for travel) with liquid in them since they are not hermetically sealed once closed.

SUMMARY

According to an embodiment, there is provided a storage box for at least one of a dental prosthesis and a dental appliance, the storage box comprising: a container portion capable of holding a liquid, the container portion comprising an opening; a holding area substantially within the container portion and for placing the at least one of a dental prosthesis and a dental appliance; a cover for placing over the opening; and an external covering material substantially covering the container portion and the cover. In this embodiment, a more robust, better looking, easier to handle and more functional storage box is provided. The covering material is convenient for it water-repellant characteristics, for the facts that it can provide a hinges for the cover and it may hide magnetic parts for ensure the cover and its flap stay closed.

According to an embodiment, there is provided a storage box for at least one of a dental prosthesis and a dental appliance, the storage box comprising: a container portion capable of holding a liquid; a holding area substantially within the container portion and for placing the at least one of a dental prosthesis and a dental appliance; and a separator dividing the holding area in two or more parts. In this embodiment, the stored parts are isolated from each other thereby reducing damage thereto. A basket with drainage holes in the holding area makes the storage box more functional easier to use.

According to another embodiment, there is provided a storage box for at least one of a dental prosthesis and a dental appliance, the storage box comprising: a container portion capable of holding a liquid, the container comprising an opening having a perimeter; a holding area substantially within the container portion and for placing the at least one of a dental prosthesis and a dental appliance; a cover comprising a groove conforming to the perimeter of the opening; and a seal held within the groove; wherein the cover closes the opening such that the perimeter interacts with the seal for hermetically sealing the opening. In this embodiment, the hermetical seal provides enhanced functionality over existing storage boxes during, for example, travel.

According to another embodiment, there is provided a storage box for at least one of a dental prosthesis and a dental appliance, the storage box comprising: a container portion capable of holding a liquid, the container comprising an opening; a holding area substantially within the container portion and for placing the at least one of a dental prosthesis and a dental appliance; and a cover having one side hinged to the container portion, the cover having an open and a closed positions, the cover comprising a lip along the one side, the lip for temporarily holding liquid in the cover when the cover is in the open position and for releasing the liquid within the opening during a passage from the open position to the closed position. In this embodiment, the inclusion of lip in the cover helps greatly in keeping the greatest quantity of liquid in the container instead of all around the storage box by the same token away from the hinge of the container and the covering material to assure a prolonged life to the container.

Features and advantages of the subject matter hereof will become more apparent in light of the following detailed description of selected embodiments, as illustrated in the accompanying figures. As will be realized, the subject matter disclosed and claimed is capable of modifications in various respects, all without departing from the scope of the claims. Accordingly, the drawings and the description are to be regarded as illustrative in nature, and not as restrictive and the full scope of the subject matter is set forth in the claims.

BRIEF DESCRIPTION OF THE DRAWINGS

Further features and advantages of the present disclosure will become apparent from the following detailed description, taken in combination with the appended drawings, in which.

It will be noted that throughout the appended drawings, like features are identified by like reference numerals.

DETAILED DESCRIPTION

Figure 1:
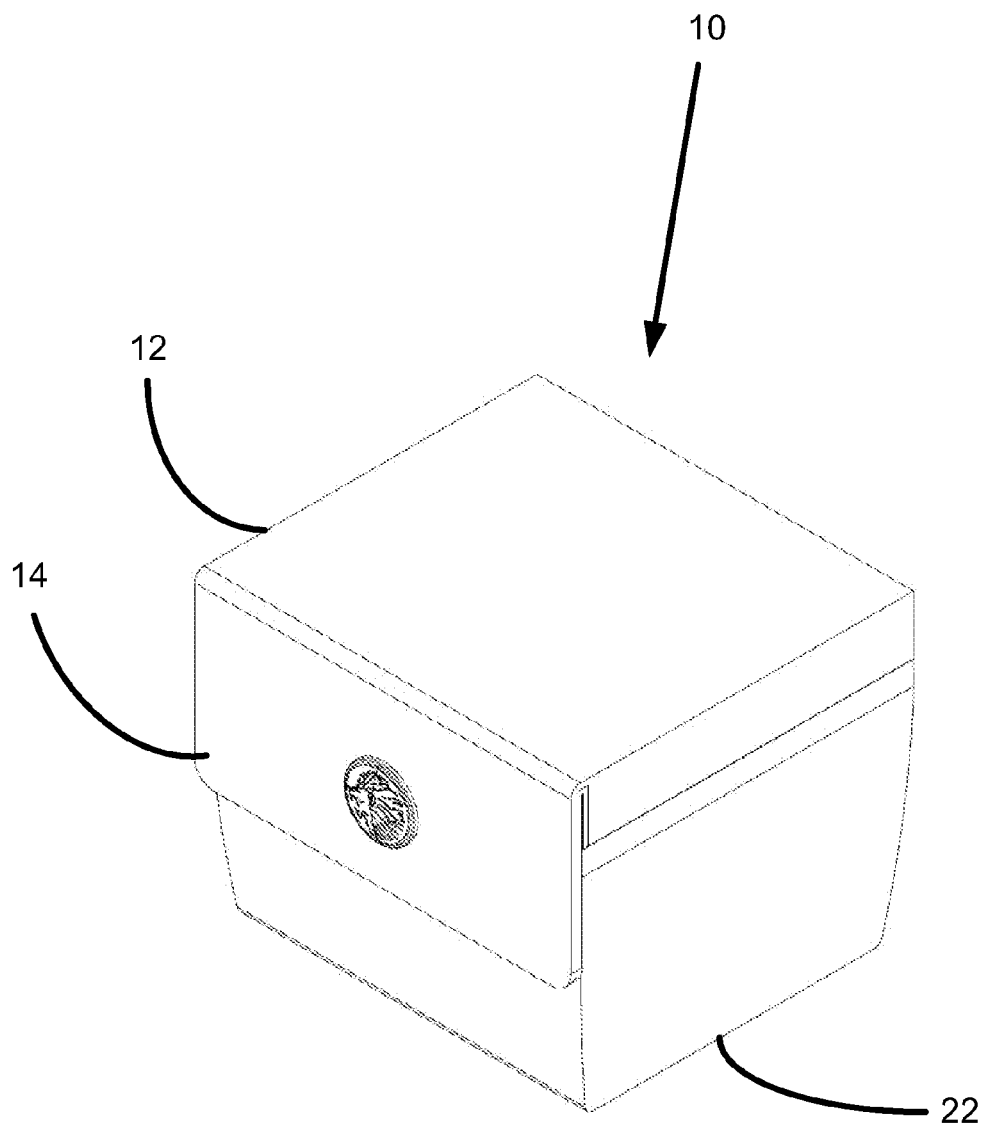
FIG. 1 is an isometric view of a dental prosthesis and dental appliance storage box in a closed state according to an embodiment of the present disclosure.

Referring now to the drawings, and more particularly to FIG. 1, there is shown a storage box 10 for a dental prosthesis and/or a dental appliance (not shown) according to an embodiment of the present disclosure. The storage box 10 comprises a cover 12 and a container portion 22. The cover is shown in a closed position (i.e., a closed state). According to an embodiment a flap 14 is hinged to the cover 12.

Figure 2:
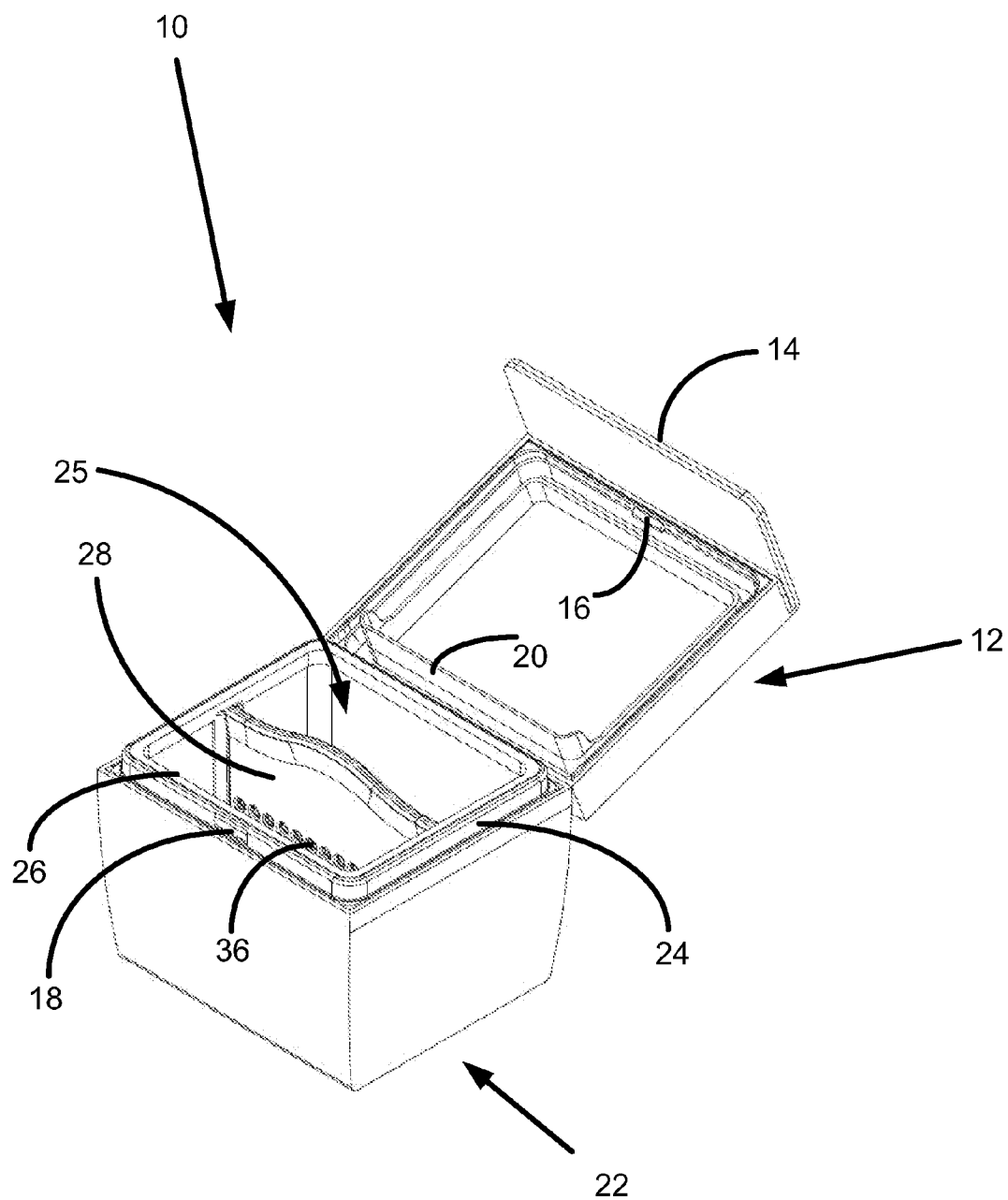
FIG. 2 is an isometric view of the box of FIG. 1 in an open state.
Figure 3A:
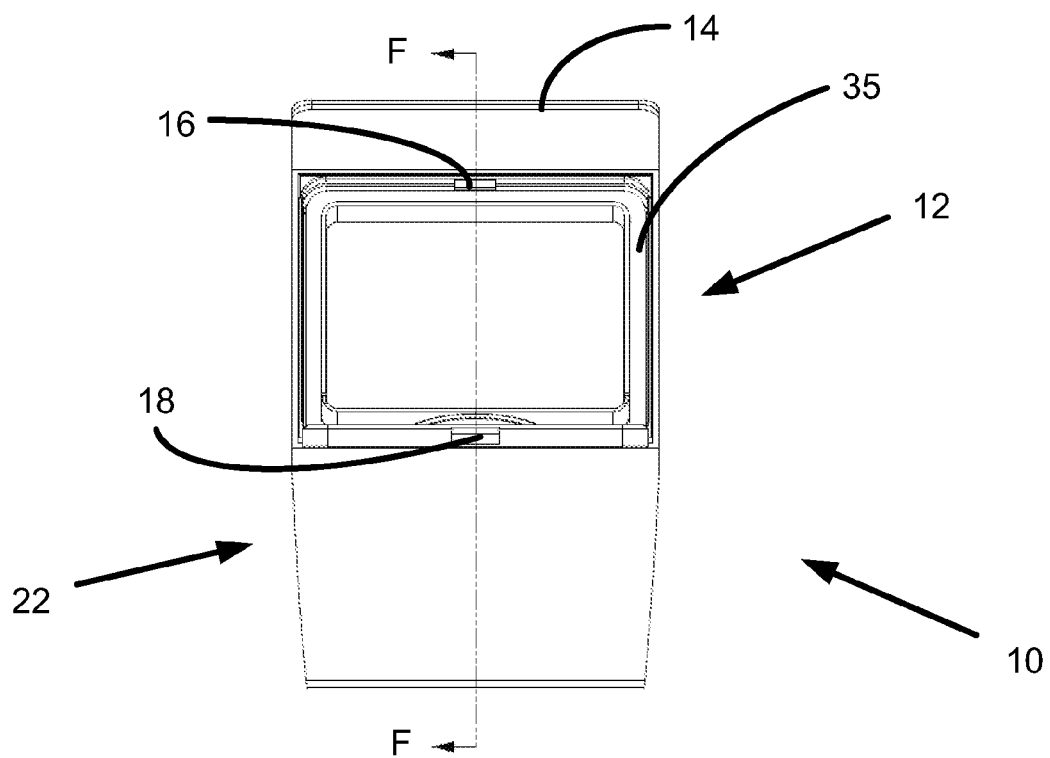
FIG. 3A is a front view in elevation of the box of FIG. 1 in an open state.
Figure 3C:
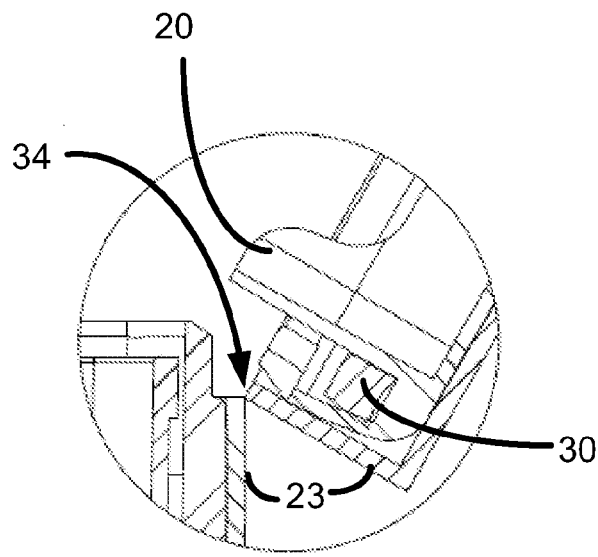
FIG. 3C is a close-up view showing the junction between the bottom portion of the box and its cover.
Figure 3B:
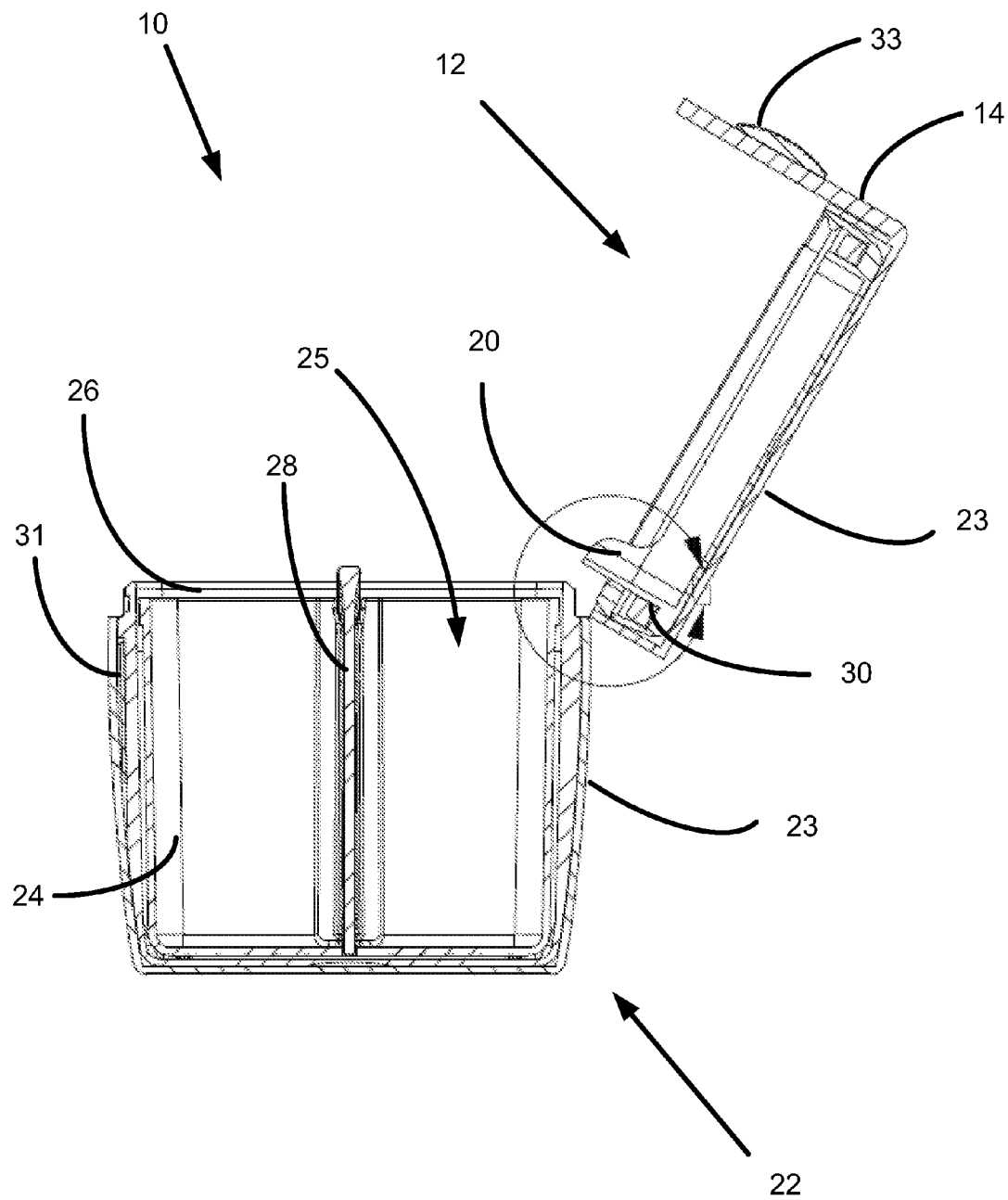
FIG. 3B is a cross-sectional view taken along line F-F of FIG. 3A.

Now referring to FIGS. 2, 3A and 3B, there is shown an embodiment of the storage box 10 of FIG. 1 with the cover open (i.e., an open state).

Storage box 10 comprises a container portion 22 capable of holding a liquid (not shown). Storage box 10 further comprises a holding area 25 substantially within the container portion 22 for placing the dental prosthesis and/or the dental appliance. According to an embodiment, an external covering material 23 substantially covers the container portion 22 and the cover 12.

According to an embodiment, a separator 28 divides the holding area 25 in two parts. According to another embodiment, the separator 28 may be configured to divide the holding area 25 into more than two parts (not shown). The number of divisions/parts required depends on the intended use.

According to an embodiment, the holding area comprises a basket 24 for removable insertion in the container portion 22. The basket 24 may comprise holes 36 for draining the liquid and a separator 28 dividing the holding area 25 in two parts. The separator 28 may comprise holes 36 permitting circulation of liquid between the separated parts.

Cover 12 may also comprise a flap 14 hinged thereto. The flap may include a magnet or metal insert 33 which interacts with another magnet (or metal insert) 31 in the container portion 22 to keep the flap against the container portion when cover 12 is in a closed position.

Cover 12 may also comprise a projection 16 which interacts with a channel 18 in the container portion 22 to lock the cover 12 on the container portion 22 thereby contributing to keeping the storage box 10 hermetically sealed.

Cover 12 may also comprise a lip 20 along the one side. The lip 20 is for temporarily holding liquid in the cover 12 when the cover is in the open position and for releasing the liquid within the opening of the container portion 22 during a passage from the open position to the closed position. The lip 20 therefore contributes to prevent damage to external covering material 23 in the area of hinge 34 (see FIG. 3C).

Now referring to FIG. 3C, there is shown a close-up view showing the junction or hinge 34 between the bottom portion of the box and its cover. FIG. 3C also shows the seal 30 in its groove 35 (see FIG. 3A) in the cover and lip 20. In this embodiment, an external covering material 23 provides the hinge 34. It should also be noted that, in the area of the hinge, the covering material can be made of liquid resistant/repellant material since liquid is likely to be present in this area and also since storage box 10 is normally handled in the presence of liquid.

Figure 4A:
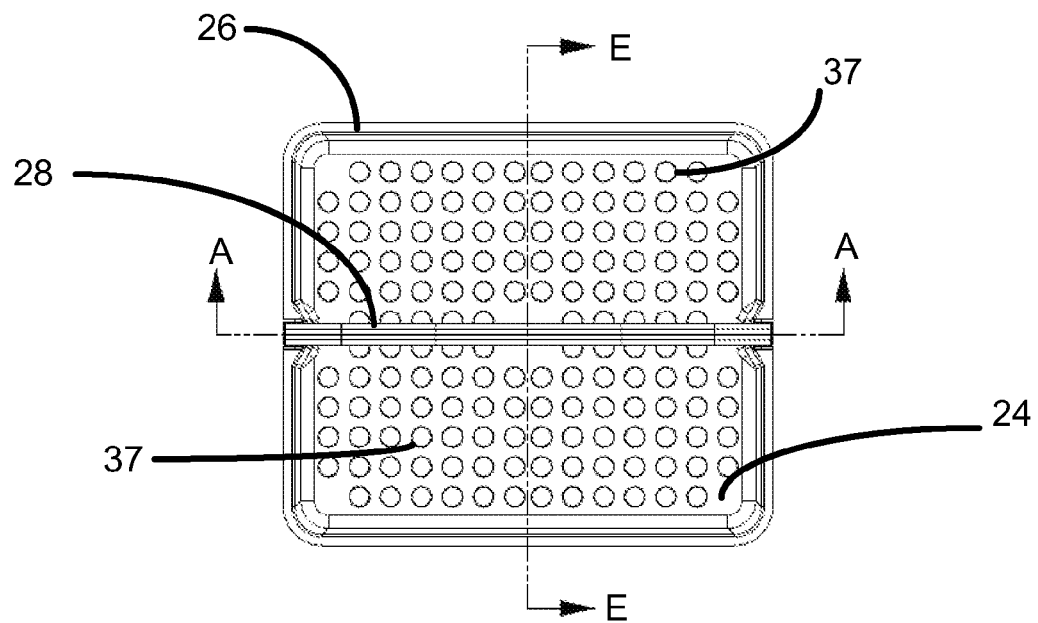
FIG. 4A is a top plan view of the inner plastic basket according to an embodiment of the present disclosure.

Now referring to FIG. 4A, there is shown a top plan view of the basket 24 according to an embodiment of the present disclosure. Basket 24 has holes 37 and a basket perimeter 26 for interacting with the groove in the cover in which seal 30 is located (see, for example, FIG. 3B). FIG. 4A also shows separator 28.

Figure 4B:
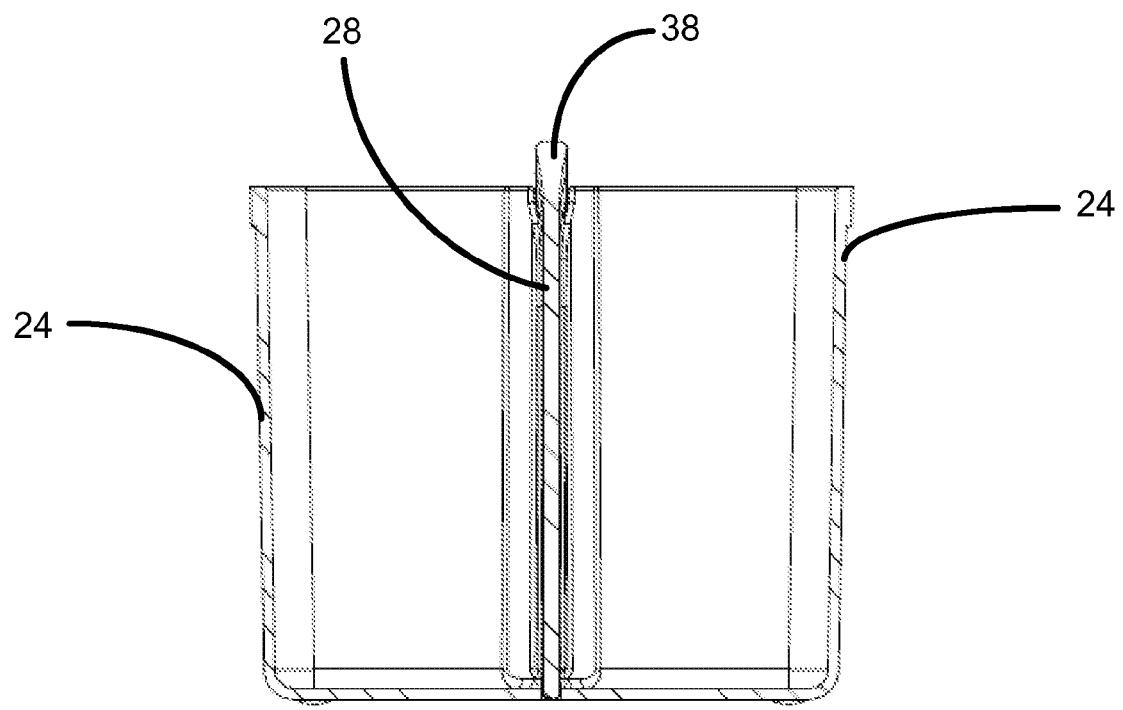
FIG. 4B is a cross-sectional view taken along line E-E of FIG. 4A showing the basket and separator.

Now referring to FIG. 4B, there is shown a cross-sectional view taken along line E-E of FIG. 4A of the basket 24 and separator 28.

Figure 5A:
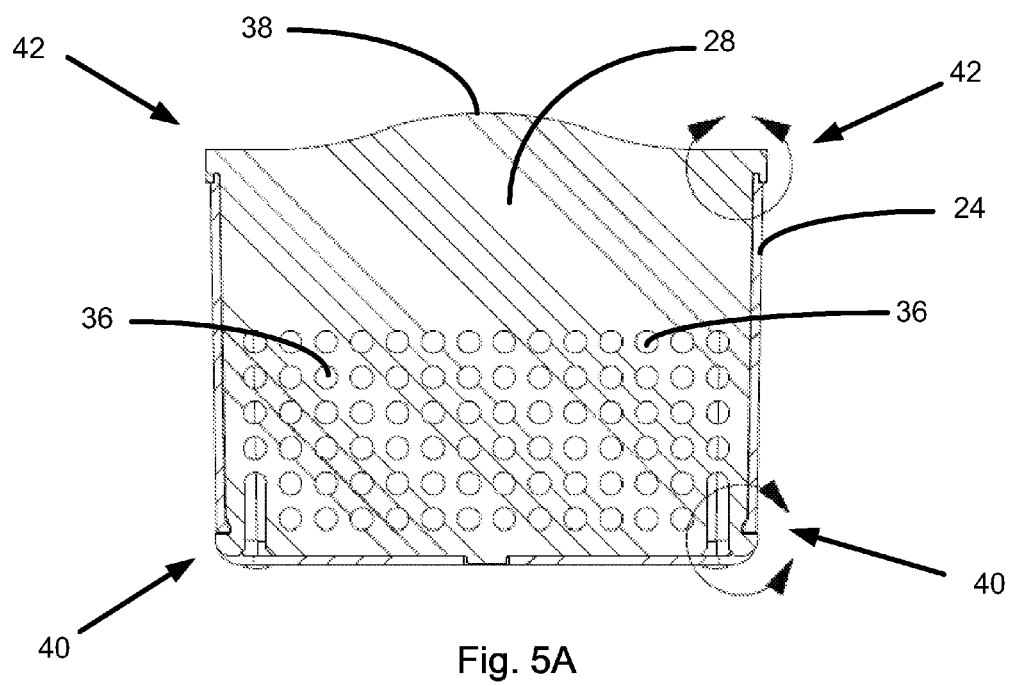
FIG. 5A is a front elevation view of the plastic in-basket separator of the dental prosthesis and dental appliance storage box according to an embodiment of the present disclosure.

Now referring to FIG. 5A, there is shown a front elevation view of the separator 28 according to an embodiment with a transversal cut-out of the basket 24. Separator 28 has holes 36, a handle 38, top corner sections 42 and bottom corner sections 40.

Figure 5B:
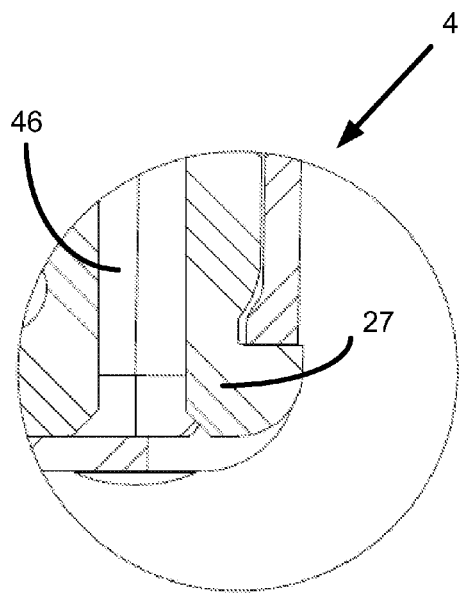
FIG. 5B is a close-up view of a lower corner of the plastic in-basket separator of FIG. 5A.

Now referring to FIG. 5B, there is shown a close-up view of a bottom corner section 40 of the separator 28 of FIG. 5A. Bottom corner section 40 comprises a locking tab 27 which fits in a slit (not shown) of basket 24. Gap 46 provides enough play in the movement of locking tab 27 such that it is possible to apply lateral pressure to locking tab 27 to unlock the separator 28 from the basket 24.

Figure 5C:
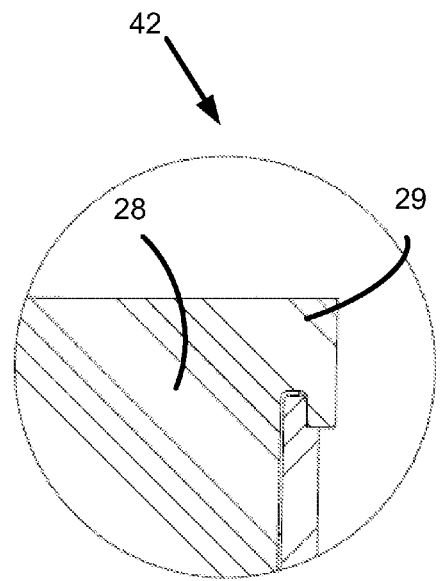
FIG. 5C is a close-up view of an upper corner of the plastic basket separator of FIG. 5A.

Now referring to FIG. 5C, there is shown a close-up view of a top corner section 42 of the basket separator 28 of FIG. 5A. Top corner section 42 comprises an overhang 29 which fits in a notch (not shown) of basket 24 for securing and preventing movement of separator 28 within basket 24.

Figure 6A:
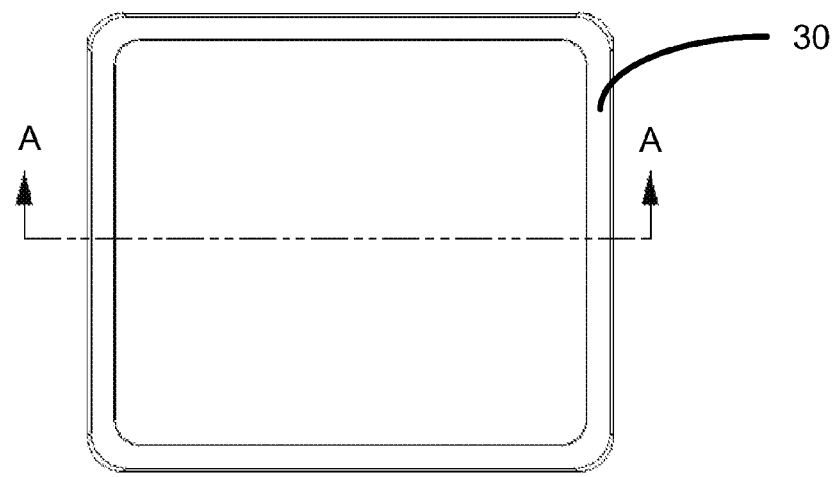
FIG. 6A is a top plan view of a seal used in the cover of the box according to an embodiment of the present disclosure.

Now referring to FIG. 6A, there is shown a top plan view of a seal 30 for placing in the cover of the box according to an embodiment of the present disclosure.

Figure 6B:
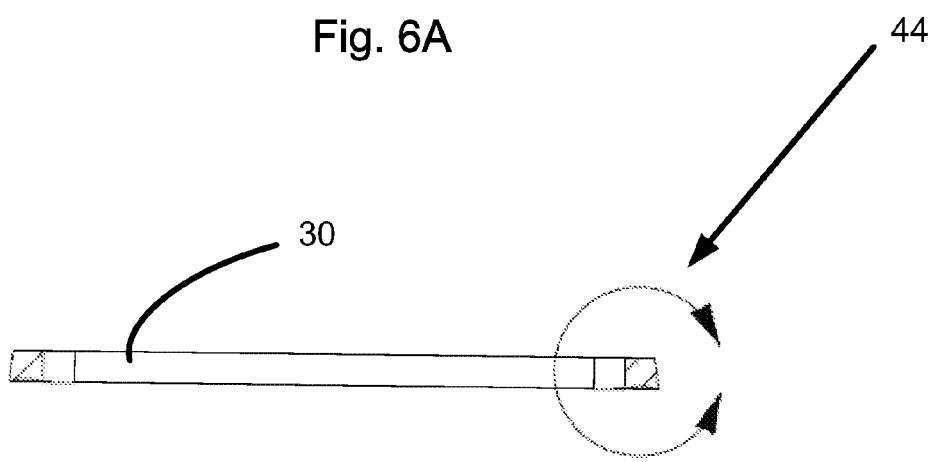
FIG. 6B is a cross-sectional view taken along line A-A of FIG. 6A.
Figure 6C:
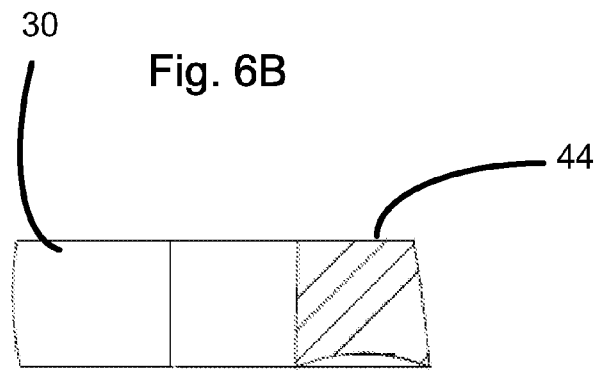
FIG. 6C is a close-up partial cross-sectional view of a portion of FIG. 6B.

Now referring to FIG. 6B, there is shown a cross-sectional view 44 taken along line A-A of FIG. 6A. Now referring to FIG. 6C, there is shown a close-up partial cross-sectional view 44 of a portion of FIG. 6B. FIG. 6C shows a better profile of seal 30. The profile of seal 30 comprises four sides, namely a top side, a bottom side, a left side and a right side. The top side is substantially flat, the bottom side is wider than the top side and is curved inwardly to the top side and the left and right sides join the top and bottom sides.

In operation, starting with the storage box 10 in a closed state, the flap 14, which is held in place by the magnets 31 and 33, is lifted and slightly pulled forward to release the projection 16 and channel 18 interaction. The cover 12 can then be freely opened by rotating it about its hinge 34 to its fully open state. Once the cover 12 is open, the dental prosthesis can be accessed if they are in the storage box 10. The basket 24 can be removed from the container portion 22 with is content by pulling on handle 38 thus avoiding contamination of the liquid solution by the user's fingers. The solution will remain in the container portion 22 since the holes in the basket 24 will let the liquid solution drip therethrough. If necessary, the liquid solution can be changed.

Upon closing the storage box 10, any liquid which has entered the cover will be kept therein until the cover 12 pivots about the hinge far enough so that the liquid solution will drop in the container. The cover 12 continues pivoting about its hinge until the projection 16 and channel 18 interact. At this point, the cover 12 must be snapped in place by pushing down on it. The flap 14 will automatically rest against the front of the container portion 22 because of the magnets 31 and 33. The storage box is then hermetically sealed and ready for travel as required.

While preferred embodiments have been described above and illustrated in the accompanying drawings, it will be evident to those skilled in the art that modifications may be made without departing from this disclosure. Such modifications are considered as possible variants comprised in the scope of the disclosure.

The invention claimed is:

1. A storage box for at least one of a dental prosthesis and an orthodontic appliance, the storage box comprising:
   a container portion capable of holding a liquid, the container portion comprising an opening;
   a holding area substantially within the container portion and adapted for placing the at least one of a dental prosthesis and an orthodontic appliance;
   a cover being reclosable and for hermetically sealing the opening thereby keeping the liquid within the storage box when the cover is closed; and an external covering material substantially covering the container portion and the cover and forming an additional contiguous layer on the outside of the container portion and the cover;

wherein the holding area comprises a basket for removable insertion in the container portion, the basket comprising holes for draining the liquid while holding the at least one of a dental prosthesis and an orthodontic appliance.

2. The storage box of claim 1, wherein the external covering material forms a hinge between the cover and the container portion.

3. The storage box of claim 2, wherein the cover comprises a side along which the hinge runs, the cover moveable between an open position and a closed position, the cover further comprising a lip along the one side, the lip for temporarily holding liquid in the cover when the cover is in the open position and for releasing the liquid within the opening during a passage from the open position to the closed position.

4. The storage box of claim 3, wherein the container further comprises a magnet or metal and the cover comprises a magnet or metal which are magnetically attracted to the magnet or metal of the container.

5. The storage box of claim 1, wherein the covering material comprises liquid resistant/repellant material.

6. The storage box of claim 1, further comprising a separator dividing the holding area in two or more parts.

7. The storage box of claim 6, wherein the separator comprises locking tab for locking the separator to the basket.

8. The storage box of claim 6, wherein the separator comprises holes.

9. The storage box of claim 1, wherein the cover comprises a groove conforming to the perimeter of the opening; and a seal held within the groove; wherein the cover closes over the opening such that the perimeter interacts with the seal for hermetically sealing the opening.

10. The storage box of claim 7, wherein the seal has a profile, the profile comprises four sides, namely a top side, a bottom side, a left side and a right side, the top side is substantially flat, the bottom side is wider than the top side and is curved inwardly to the top side and the left and right sides join the top and bottom sides.

11. The storage box of claim 1, wherein the container portion further comprises a channel and the cover further comprises a projection which interacts with the channel to lock the cover on the container portion.

* * * * *